(12) United States Patent
Chen et al.

(10) Patent No.: US 10,456,426 B2
(45) Date of Patent: Oct. 29, 2019

(54) EGG CHALAZA HYDROLYSATE, METHOD FOR PREPARING THE SAME AND USAGE OF THE SAME

(71) Applicant: NATIONAL TAIWAN UNIVERSITY, Taipei (TW)

(72) Inventors: Yi-Chen Chen, Taipei (TW); Yu-Xuan Lin, New Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/658,792

(22) Filed: Jul. 25, 2017

(65) Prior Publication Data
US 2018/0117094 A1    May 3, 2018

(30) Foreign Application Priority Data
Oct. 27, 2016    (TW) .............................. 105134785 A

(51) Int. Cl.
| C12P 21/06 | (2006.01) |
| A61K 35/57 | (2015.01) |
| A61K 9/00 | (2006.01) |
| A61K 31/198 | (2006.01) |
| A61K 31/401 | (2006.01) |
| A61K 31/405 | (2006.01) |
| A61K 31/661 | (2006.01) |
| A61K 38/01 | (2006.01) |
| A61K 38/05 | (2006.01) |

(52) U.S. Cl.
CPC ............ *A61K 35/57* (2013.01); *A61K 9/0053* (2013.01); *A61K 31/198* (2013.01); *A61K 31/401* (2013.01); *A61K 31/405* (2013.01); *A61K 31/661* (2013.01); *A61K 38/012* (2013.01); *A61K 38/05* (2013.01); *C12P 21/06* (2013.01); *C12Y 304/21063* (2013.01)

(58) Field of Classification Search
None
See application file for complete search history.

(56) References Cited

FOREIGN PATENT DOCUMENTS

| CN | 101366440 B | 3/2011 | |
| JP | 5735734 B2 | 6/2015 | |
| TW | I425004 B | 2/2014 | |
| TW | I437999 B | 5/2014 | |
| WO | WO-2016022917 A2 * | 2/2016 | ............ A61K 35/36 |

OTHER PUBLICATIONS

Jeng Huang; Studies on the antioxidive mechanism and properties in the O/W emulsion of hen's egg enzymatic hydrolysates, 2005.*
Mizuno et al. Royal Society of Chemistry, Metallomics, 2015, 7, 1233-1239.*
Ito et al. J Nutr Diet Pract. vol. 1(1): 2017; Ueno H (2017) Free Amino Acid Compositions for Fruits that occur naturally; Table 2; See also, Huang showing the occurrence of said amino acids in egg chalaza proteins.*
Hsin-Yi Chen; Master Thesis; "Studies on the Antioxidative Mechanism and Antioxidant Activities in O/W Emulsion of Hen's Egg Enzymatic Hydrolysates"; Department of Food Science National Chiayi University, Jun. 2005.
Kang Chi, "Five Kinds of Liver Protection Drugs"; https://kknews.cc/health/aqmbvn.html, pp. 1-2, Oct. 12, 2016.

* cited by examiner

*Primary Examiner* — Jeanette M Lieb
(74) *Attorney, Agent, or Firm* — Rosenberg, Klein & Lee

(57) ABSTRACT

An egg chalaza hydrolysate, a method for preparing the same and a usage of the same are revealed. An egg chalaza is hydrolyzed by an enzyme to get a hydrolysate solution. The hydrolysate solution is filtered and lyophilized to get an egg chalaza hydrolysate. The egg chalaza hydrolysate includes leucine, arginine, phenylalanine, valine, and lysine. The egg chalaza hydrolysate can reduce fat accumulation and oxidative stress in livers. Thus the egg chalaza hydrolysate is applied to prepare a composition for liver protection.

3 Claims, 11 Drawing Sheets
(2 of 11 Drawing Sheet(s) Filed in Color)

EGG CHALAZA HYDROLYSATE, METHOD FOR PREPARING THE SAME AND USAGE OF THE SAME

BACKGROUND OF THE INVENTION

Field of the Invention

The present invention relates to an egg chalaza hydrolysate, a method for preparing the same and a usage of the same, especially to an egg chalaza hydrolysate that is prepared by a specific method and able to reduce fat accumulation and hepatic oxidative stress in livers effectively.

Descriptions of Related Art

Egg is a food with low cost and high nutritional value, and able to be used for preparation of other food. Thus the egg is essential in our daily lives. Liquid eggs refer to chicken eggs that have been broken out of their shells to be sold in a liquid form. The liquid egg products include liquid whole egg, liquid egg yolk and liquid egg whites. The liquid egg is pasteurized at a lower temperature during a preparation process for food safety. Chalaza is a structure inside eggs and used to keep the yolk in place. The chalaza contains a plenty of proteins. Yet the chalaza is filtered off along with bits of shells during the preparation of the liquid eggs.

Food protein hydrolysates are products after hydrolysis of food containing proteins. The hydrolysates include various amino acids or peptides and some of them even have healthcare function. Refer to Japanese Pat. No. 5735734 (B2), a whey protein hydrolysate (WPH) is revealed. The WPH contains peptides or free amino acids with molecular weight smaller than 10 kDa that are able to improve lipid metabolism. Refer to Taiwanese Pat. No. TW 1425004 (B), bioactive hydrolysates prepared from pork livers and used for inhibiting body weight are revealed. The products obtained by hydrolysis of pork liver with enzymes can stimulate secretion of cholecystokinin and further inhibit the appetite. Thus the body weight is reduced. Also refer to Taiwanese Pat. No. TW 1437999 (B), antioxidative oligosaccharide peptides are disclosed. Crude extract of mushrooms (such as *Taiwanofungus camphoratus*) is hydrolyzed to get antioxidative oligosaccharide peptides. Yet the raw materials used and the hydrolysis steps all affect the properties of the final hydrolysates obtained.

Since the egg chalaza is having a plenty of proteins and not used properly, there is a need to find out the usage of the egg chalaza.

SUMMARY OF THE INVENTION

Therefore it is a primary object of the present invention to provide an egg chalaza hydrolysate that includes 90-120 mg/g free amino acids. The free amino acids comprise 10-20 wt % leucine, 7-14 wt % arginine, 8-10 wt % phenylalanine, 8-10 wt % valine, and 8-10 wt % lysine.

It is another object of the present invention to provide a method for preparing an egg chalaza hydrolysate that includes the following steps. Step 1: First defrost an egg chalaza and wash with distilled deionized water for removal of impurities. Take a first product at a lower layer after centrifugation. Step 2: Heat the first product at 95° C. for 10-30 minutes and cool down. Then add distilled deionized water to get a homogeneous solution of the egg chalaza. Step 3: Mix 100-200 g homogeneous solution of the egg chalaza with a hydrolase at a ratio of 100:1-500:1 (w/w). After reacting a period of time, a first hydrolysate solution is obtained. Step 4: Heat the first hydrolysate solution at 95° C. for 10-30 minutes and cool down. Then take a second hydrolysate solution at an upper layer after centrifugation. Step 5: Filter and lyophilize the second hydrolysate solution to get an egg chalaza hydrolysate.

It is a further object of the present invention to provide an egg chalaza hydrolysate used for preparing a composition for liver protection. An effective dose of the composition prepared applied to a subject can reduce fat accumulation or hepatic oxidative stress in livers for the liver protection. The egg chalaza hydrolysate includes 90-120 mg/g free amino acids. The free amino acids comprise 10-20 wt % leucine, 7-14 wt % arginine, 8-10 wt % phenylalanine, 8-10 wt % valine, and 8-10 wt % lysine.

The egg chalaza hydrolysate includes 15.47% leucine, 10.89 wt % arginine, 9.74 wt % phenylalanine, 9.64 wt % valine and 9.09 wt % lysine.

The egg chalaza hydrolysate further includes carnosine, anserine or their combinations.

The carnosine is ranging from 20-60 mg/100 g and anserine is ranging from 95-150 mg/100 g, or their combinations.

The hydrolase includes at least one of the followings: pepsin, protease A, and prozyme 6. The ratio of enzyme to substrate is 1:200 (w/w) and the reaction time is 30 minutes.

The hydrolase used is protease A.

The fat accumulated in the liver is triglyceride or total cholesterol.

The egg chalaza hydrolysate prepared by a specific method of the present invention can be used to reduce fat accumulation and hepatic oxidative stress in livers for liver protection.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
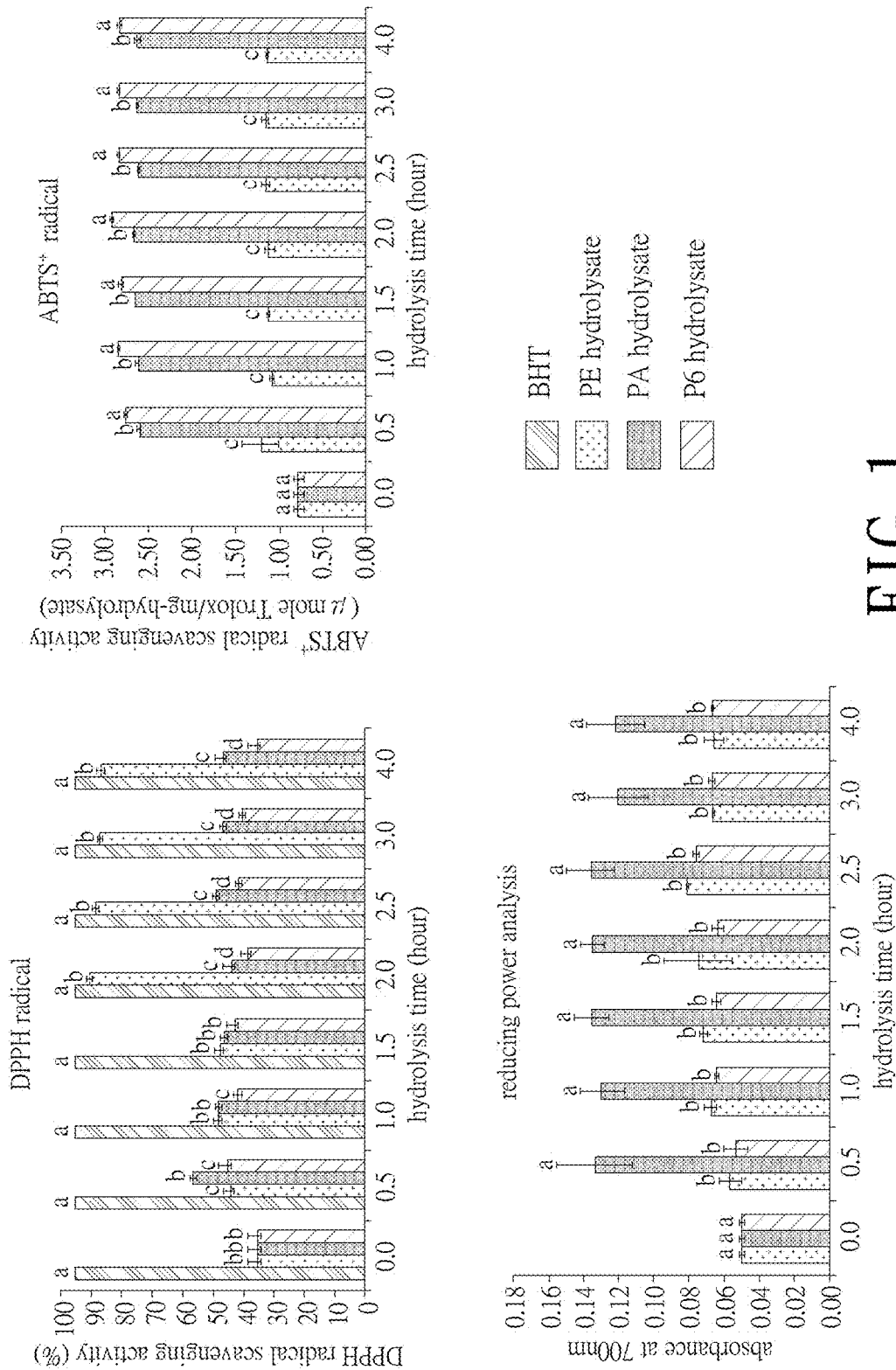
FIG. 1 shows bar charts of in vitro antioxidant activities of egg chalaza hydrolysates prepared by enzymes with the same ratio of enzyme to substrate according to the present invention.

In order to learn functions and details of the present invention, please refer to the following embodiments and related figures.

The present invention relates to an egg chalaza hydrolysate that contains free amino acids ranging from 90 mg/g to 120 mg/g. The free amino acids comprise 10-20 wt % leucine, 7-14 wt % arginine, 8-10 wt % phenylalanine, 8-10 wt % valine, and 8-10 wt % lysine. The egg chalaza hydrolysate further includes either carnosine ranging from 20-60 mg/100 g, anserine ranging from 95-150 mg/100 g, or their combinations.

A method for preparing an egg chalaza hydrolysate according to the present invention includes the following steps.
Step 1: First defrost an egg chalaza and wash with distilled deionized water for removal of impurities. Take a first product at a lower layer after centrifugation.
Step 2: Heat the first product at 95° C. for 10-30 minutes and cool down. Then add distilled deionized water to get a homogeneous solution of the egg chalaza.
Step 3: Mix 100-200 g of the homogeneous solution with a hydrolase at a ratio of 100:1-500:1 (w/w). After reacting a period of time, get a first hydrolysate solution.
Step 4: Heat the first hydrolysate solution at 95° C. for 10-30 minutes and cool down. Then take a second hydrolysate solution at an upper layer after centrifugation.
Step 5: filter and lyophilize the second hydrolysate solution to get an egg chalaza hydrolysate. The hydrolase includes at least one of the followings: pepsin, protease A, and prozyme 6. The ratio of enzyme to substrate is 1:200 (w/w) and the reaction time is 30 minutes.

The egg chalaza hydrolysate of the present invention can be applied to prepare a composition for liver protection. Applying an effective dose of the composition to a subject can reduce lipid accumulation or oxidative stress in livers. The egg chalaza hydrolysate includes 90-120 mg/g free amino acids. The free amino acids comprise 10-20 wt % leucine, 7-14 wt % arginine, 8-10 wt % phenylalanine, 8-10 wt % valine, and 8-10 wt % lysine. The lipid reduced by the egg chalaza hydrolysate includes triglyceride (TG) and total cholesterol (TC).

Please refer to the following embodiments for more details.

EXPERIMENT ONE

Preparation of Egg Chalaza Hydrolysate

Crude chalazae used in the experiment are provided by Daiegg Co. Ltd., Tainan city, Taiwan. After being collected from the liquid egg production line and frozen at −18° C. for storage and transportation, the chalazae are delivered to the animal health product and meat product lab, Department of Animal Science and Technology, National Taiwan University, Taiwan, R.O.C. and frozen at a −20° C. freezer. After defrosting, removal of impurities and water-washing, the solution is centrifuged at 900 g for 15 minutes and a lower layer with the chalazae is collected. Then the chalaza solution is placed into a circulating water bath at 95° C. for 15 minutes to inactivate endogenous enzymes in the chalazae. After water bath, the sample is placed on ice and cooled down to room temperature. Add distilled deionized water ($ddH_2O$) whose weight is two times the weight of the sample and homogenize with a homogenizer for 1 minute to get a homogeneous solution of the egg chalazae. Next leave the homogeneous solution of the egg chalazae in a 4° C. refrigerator for removal of bubbles generated during the homogenization.

Take 150 g of the homogeneous solution of the egg chalazae (containing 50 g egg chalazae and 100 g $ddH_2O$) and adjust the pH value and temperature of the homogeneous solution of the egg chalazae to optimal conditions for enzymes. The enzymes used include pepsin (PE), protease A (PA) and prozyme 6 (P6). The properties of the three enzymes are shown in Table 1. Mix the enzyme with the homogeneous solution of the egg chalazae in the ratio of enzyme to substrate ranging from 1:100 (w/w) to 1:500 (w/w) and carry out hydrolysis after the temperature and the pH value of the homogeneous solution of the egg chalazae reach the optimal conditions. The hydrolysis takes 4 hours and then the hydrolysate is collected at 0.5 hour, 1 hour, 1.5 hours, 2 hours, 2.5 hours, 3 hours and 4 hours after starting hydrolysis respectively. The hydrolysis is terminated by heating at 95° C. for 15 minutes. Cool down and centrifuge the homogeneous solution at 900 g, 4° C. for 15 minutes and collect an upper layer of homogeneous. The upper layer of homogeneous was filtered with 55 mm filter paper to get a filtrate and the pH value of the filtrate was adjusted to 7.0. An egg chalaza hydrolysate was obtained by freeze-drying the pH value-adjusted filtrate. The egg chalaza hydrolysate is stored at −20° C. and the free radical scavenging ability of the egg chalaza hydrolysates was analyzed. The analyzing results are used as criteria for selecting methods for preparing the egg chalaza hydrolysate. In order to differentiate the egg chalaza hydrolysates prepared by the above three enzymes, the egg chalaza hydrolysates prepared by different enzymes are called PE hydrolysate, PA hydrolysate, and P6 hydrolysate respectively.

TABLE 1

| | | optimal conditions | | |
|---|---|---|---|---|
| enzyme | source | pH value | temperature | activity |
| pepsin (PE) | porcine stomach mucosa | pH = 2 | 37° C. | 3,000,000 unit/g |
| protease A (PA) | Aspergillus oryzae | pH = 6 | 50° C. | 63,000 unit/g |
| prozyme 6 (P6) | Aspergillus melleus | pH = 8 | 45° C. | 748,000 unit/g |

EXPERIMENT TWO

Analysis of In Vitro Antioxidant Activity of Egg Chalaza Hydrolysate 2.1 DPPH Radical Scavenging Activity DPPH (2,2-diphenyl-1-picrylhydrazyl) is a free radical (peroxyl radical) that produces violet color in ethanol. An ethanol solution of DPPH has a strong absorption band at a wavelength of 517 nm. Once a test sample with an antioxidant activity that donates hydrogen, DPPH is reduced and the optical density (OD) at 517 nm (OD 517) is decreased.

The lower the OD 517 is measured means the test sample has the higher hydrogen-donating ability and the higher antioxidant activity. The experiment is performed according to the following steps. 200 μL of the egg chalaza hydrolysate is mixed evenly with 100 μL of 1 mM DPPH in ethanol solution in a 96-well plate and reacts for 30 minutes. The OD 517 of the samples at 517 nm is detected by an ELISA (enzyme-linked immunosorbent assay) reader. The whole experiment should be kept away from light. The Dibutyl Hydroxy-Toluene (BHT) ethanol solution (1 mg/mL) is a positive control for the experiment, and 95% ethanol is a negative control. Compare DPPH radical scavenging activity of the test samples with that of the positive and negative controls. The DPPH radical scavenging activity is calculated using the following equation:

DPPH radical scavenging activity (%)=(1−OD517 value of the test sample/OD517 value of the negative control)×100%

2.2 ABTS$^+$ Radical Scavenging Activity

When reacts with $H_2O_2$ and peroxidase, ABTS[2,2'-azino-bis(3-ethylbenzthiazoline-6-sulphonic acid)] transforms to blue-green colored ABTS$^+$ free radicals and has a strong absorption band at 734 nm. The generation of ABTS$^+$ free radicals/blue-green color is inhibited by the test sample with antioxidant activity and this leads to decrease in the absorbance measured at 734 nm. The test method includes the following steps. Preparation of a ABTS solution contains 5 mL ABTS (1 mM), 5 mL peroxidase (44 U/mg), 5 mL 10% $H_2O_2$ and 30 mL dd$H_2O$, and the ABTS solution is keep away from light for 60 minutes. 20 μL of the test sample is mixed with 200 μL of the ABTS solution, after 10 minutes, the absorbance of the test sample at 734 nm is measured to obtain the OD734 value. A standard curve is created by performing the above reaction with different concentration of Trolox, an analog of vitamin E. Then compare the OD734 value of the test sample and the standard curve to calculate trolox equivalent antioxidant capacity (TEAC). The trolox equivalent antioxidant capacity (TEAC) that measures antioxidant strength based on trolox is calculated in units called Trolox Equivalents (TE), e.g. μmol trolox/mg-hydrolysate.

2.3 Reducing Power Analysis

The substances with antioxidant activity can reduce potassium ferricyanide ($K_3[Fe(CN)_6]$) with ferric ions into potassium ferrocyanide (($K_4[Fe(CN)_6].3H_2O$)) with ferrous ions and further react with ferric chloride ($FeCl_3$) to form Prussian blue that has a maximum absorption at 700 nm. The reducing power of the test sample is learned by measurement of the amount of Prussian blue. The higher the absorbance at 700 nm (OD700) measured, the better the reducing power the test sample has. 500 μL of the test sample is added into 250 μL 0.2 M phosphate buffered saline and 250 μL 1% potassium ferricyanide aqueous solution, and the mixture above is mixed evenly to get a first mixture. and place the first mixture is incubated in 50° C. water bath for 15 minutes, then cool down the first mixture to room temperature quickly on ice. The first mixture is mixed well with 250 μL of 10% trichloroacetic acid (TCA) aqueous solution and centrifuge. A supernatant is collected and 500 μL of the supernatant is mixed with 250 μL dd$H_2O$ and 500 μL 0.1% ferric chloride aqueous solution to obtain a second mixture. Mixing the second mixture well and leaving for 10 minutes, then the absorbance of the test sample at 700 nm is measured. BHT ethanol solution (1 mg/mL) is used as positive control and compared with the sample of the egg chalaza hydrolysate.

2.4 Ferrous Ion Chelating Ability Assay

Metal ions promote oxidation by acting as pro-oxidants and further increase the odds of lipid peroxidation. Ferrous ions are the most powerful pro-oxidant among the various species of metal ions. Small number of ferrous ions is able to promote free radical formation and accelerate lipid oxidation. In antioxidant research, ferrous ions react with ferrozine to form complexes having color reaction at 562 nm. The ferrous ion chelating ability of the test sample can be estimated by concentration measurement of the complexes. If the test sample forms complex with ferrous ions, the color reaction at 562 nm will be reduced. The protocol of chelating ability assay is simple describes below. 250 μL samples with different concentrations or 250 μL of controls is mixed with 3.7 mL methanol first, and then mixed with 0.1 mL of 2 mM $FeCl_2$ to get a $FeCl_2$ mixture. After 30 seconds, 0.2 mL of 5 mM ferrozine was added into the $FeCl_2$ mixture and react for 10 minutes. At last, the absorbance of the test samples and controls at 562 nm are measured. Ethylenediaminetetraacetic acid (EDTA) aqueous solution and dd$H_2O$ are used as positive control and negative control respectively. The lower absorbance at 562 nm is means the higher ferrous ion chelating ability of the test sample has. The ferrous ion chelating ability is calculated using the following equation:

chelating ability (%)=[1−(OD562 value of the test sample/OD562 value of the negative control)]×100%

The data obtained is statistically analyzed by analysis of variance (ANOVA) and then least significant difference (LSD) is used to compare differences between any two groups. In the analysis chart, if there is no significant difference between the two groups so that they are classified into the same group and labeled with the same small letter. Some groups are labeled with ab, it means there is no significant difference between these groups and the group a. There is also no significant difference between these groups and the group b. Thus they are classified into both the group a and the group b.

Refer to FIG. 1, analysis results of the DPPH radical scavenging activity of the egg chalaza hydrolysates prepared by three different enzymes with the same ratio of enzyme to substrate (1:200), compared with that of BHT are shown in the figure. The DPPH radical scavenging activity of unhydrolyzed egg chalaza (hydrolysis time 0 hr) is 35.12%, and the DPPH radical scavenging activity of the egg chalaza hydrolysates is significantly increased along with the increasing hydrolysis time. At the same hydrolysis time, PE hydrolysate has the highest DPPH radical scavenging activity and the ability is increased along with the hydrolysis time. The PE hydrolysate obtained after two hours of hydrolysis has the highest DPPH radical scavenging activity, 90.14%. The PA hydrolysate obtained after 0.5 hour hydrolysis has the highest DPPH radical scavenging activity, 56.3%. The P6 hydrolysate obtained after 0.5 hour hydrolysis has the highest DPPH radical scavenging activity, 45.24%.

As to the ABTS$^+$ radical scavenging activity of unhydrolyzed egg chalaza (hydrolysis time 0 hr), it's only 0.79 μmole TE/mg-raw material for chalaza. After hydrolysis, the ABTS$^+$ radical scavenging activity of the three hydrolysates is dramatically increased. The ABTS$^+$ radical scavenging activity of each group reaches the highest level at the reaction time of 0.5 hour. Among them, P6 hydrolysate gets the best performance. The ABTS$^+$ radical scavenging activity of P6 hydrolysate is 2.91 μmole TE/mg-egg chalaza hydrolysate after 0.5 hours hydrolysis. The next is the PA hydroysate, 2.60 µmole TE/mg-egg chalaza hydrolysate. The ABTS$^+$ radical scavenging activity of PE hydrolysate, 1.20 µmole TE/mg-egg chalaza hydrolysate, is significantly lower than the rest two groups (p<0.05).

In the reducing power analysis, the absorbance of the egg chalaza at 700 nm before hydrolysis is 0.05. After being treated by three enzymes, the reducing power of the egg chalaza hydrolysate is improved. The highest reducing power is seen in the PA hydrolysate group whose absorbance is 0.13 after 0.5 hour hydrolysis, significantly higher than the rest two groups (p<0.05). The PE hydrolysate group and P6 hydrolysate group have similar reducing power. Both groups reach the maximum absorbance 0.06 after 2 hour hydrolysis and have poor performance.

Since the three enzymes used in the present invention for chalaza hydrolysation have different activities, the activity of PE is 3,000,000 unit/g, the activity of PA is 63,000 unit/g and the activity of P6 is 748,000 unit/g, when the radio of enzyme to substrate is the same in different groups, the enzyme added has different units. In order to make the test more objective, the egg chalaza hydrolyzation with the same unit of the three enzymes and the analysis of in vitro antioxidant activity of egg chalaza hydrolysate were performed again. The enzyme unit used in this experiment is 795 unit/g-egg chalaza (raw material) and the hydrolysis time is 0.5 hour.

Figure 2:
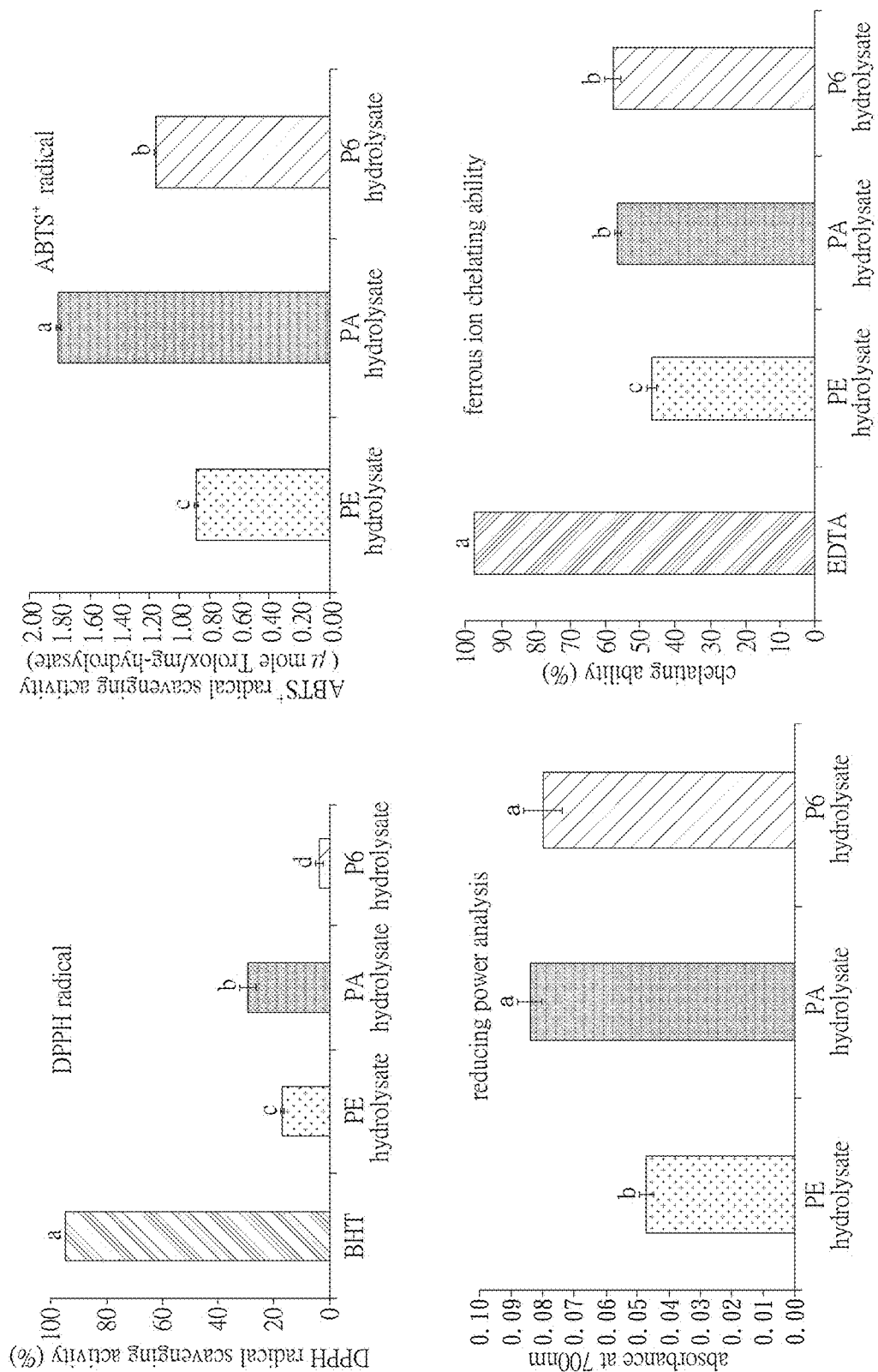
FIG. 2 shows bar charts of in vitro antioxidant activities of egg chalaza hydrolysates prepared by enzymes with the same unit according to the present invention.

As shown in FIG. 2, compared with BHT, the DPPH radical scavenging activity of the PE hydrolysate group, the PA hydrolysate group, and the P6 hydrolysate group, is 16.93%, 29.25% and 3.46% respectively. As to the ABTS$^+$ radical scavenging activity, the PA hydrolysate group gets the best performance, 1.81 µmole TE/mg-hydrolysate. The second is 1.15 µmole TE/mg-hydrolysate of the P6 hydrolysate group and the worse is 0.89 µmole TE/mg-hydrolysate of the PE hydrolysate group. That means the PA hydrolysate group has the highest ABTS$^+$ radical scavenging activity with the same enzyme activity (795 unit/g-egg chalaza (raw material)). The results of the reducing power analysis show that the PA hydrolysate group and the P6 hydrolysate group have a higher reducing power than the PE hydrolysate group.

As shown in FIG. 2, compared with EDTA, the ferrous ion chelating ability of the PA hydrolysate and that of the P6 hydrolysate are 56.60% and 57.96%, respectively while the ferrous ion chelating ability of the PE hydrolysate is 46.69%, obviously lower than the rest two groups (p<0.05).

The protease A has both exopeptidase and endoprotease activities. The analysis results of in vitro antioxidant activity of egg chalaza hydrolysate show that PA hydrolysate gives good performance in the DPPH radical scavenging activity, the ABTS$^+$ radical scavenging activity, the ferrous ion chelating ability assay and the reducing power analysis. Thus protease A is used in the following preparation of the egg chalaza hydrolysates.

In order to find out the optimal ratio of enzyme to substrate for hydrolyzation of the chicken chalaza in the the present invention, the in vitro antioxidant activity of egg chalaza hydrolysate prepared by the ratio of enzyme to substrate ranging from 1:100 to 1:500 is tested.

Figure 3:
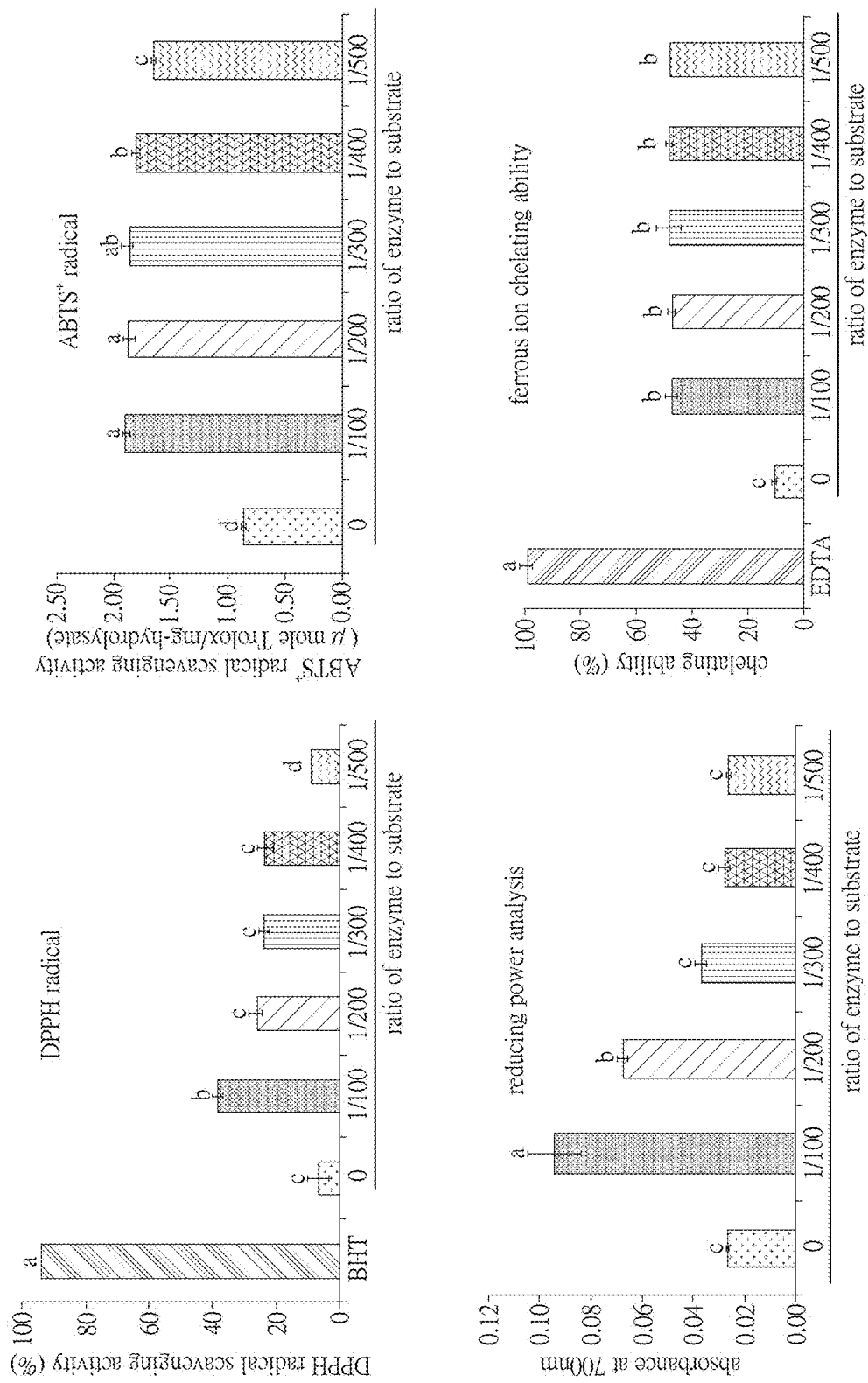
FIG. 3 shows bar charts of in vitro antioxidant activities of egg chalaza hydrolysates prepared by protease A with different ratio of enzyme to substrate according to the present invention.

Refer to FIG. 3, the DPPH radical scavenging activity of the PA hydrolysate with the ratio of enzyme to substrate 1:100 is 38.24% and is decreased along with the lower ratio of enzyme to substrate (1:200, 1:300, 1:400 and 1:500). The DPPH radical scavenging activity of the PA hydrolysates with the ratio of enzyme to substrate 1:200, 1:300, 1:400 and 1:500 is 26.47%, 23.71%, 23.38%, and 8.99% respectively. Similarly, the ABTS$^+$ radical scavenging activity of the PA hydrolysates with the ratio of enzyme to substrate 1:100, 1:200, 1:300, 1:400 and 1:500 is 1.90, 1.87, 1.85, 1.80, and 1.63 µmole TE/mg-PA hydrolysate. The reducing power analysis has similar results. The PA hydrolysate with the highest ratio of enzyme to substrate gets the best reducing power and has the absorbance of 0.094 at 700 nm. The absorbance of the PA hydrolysates is decreased along with the lowered ratio of enzyme to substrate. The absorbance of the PA hydrolysates with higher to lower ratio of enzyme to substrate is 0.067, 0.036, 0.027 and 0.026 in turn. As to the ferrous ion chelating ability assay, the chelating ability of the five PA hydrolysates with different ratio is similar to one another. The chelating ability of the PA hydrolysates from higher to the lower ratio of enzyme to substrate is 47.14%, 46.78%, 47.80%, 47.95%, and 47.47% in turn, respectively.

EXPERIMENT THREE

Peptide Amount Analysis

The amount of peptide the egg chalaza hydrolysate contained is used to evaluate hydrolysis ability of the enzyme and estimate the amount of peptide the test sample contained. When O-phthalaldehyde (OPA) and β-mercaptoethanol (β-ME) react with a primary amine, a fluorescent substance with blue color and a strong absorption band at 340 nm has produced. The fluorescent substance with blue color is used as an indicator for estimation of the amount of peptide in samples. First, 40 mg of OPA is dissolved in 1 mL methanol to get a OPA methanol solution. The OPA methanol solution is then mixed with 25 mL 100 mM sodium tetraborate decahydrate, 2.5 mL 20% sodium dodecyl sulfate (SDS) and 100 µL β-ME evenly, and the total volume of this mixture is brought to 50 mL by adding ddH$_2$O to obtain aOPA reagent. To create a standard curve, 10 µL of glycine-glycine aqueous solution with different concentrations (100 mg/mL, 50 mg/mL, 25 mg/mL, 12.5 mg/mL, 10 mg/mL and 1 mg/mL) and 200 µL OPA reagent were inject into a 96-well plate and react for 2 minutes, and measure the absorbance at 340 nm is measured. The diluted test sample is added and reacted with the OPA reagent and the the absorbance at 340 nm was measured as mentioned above. The amount of peptide can be estimated by comparing the absorbance of the test sample with the standard curve.

Figure 4:
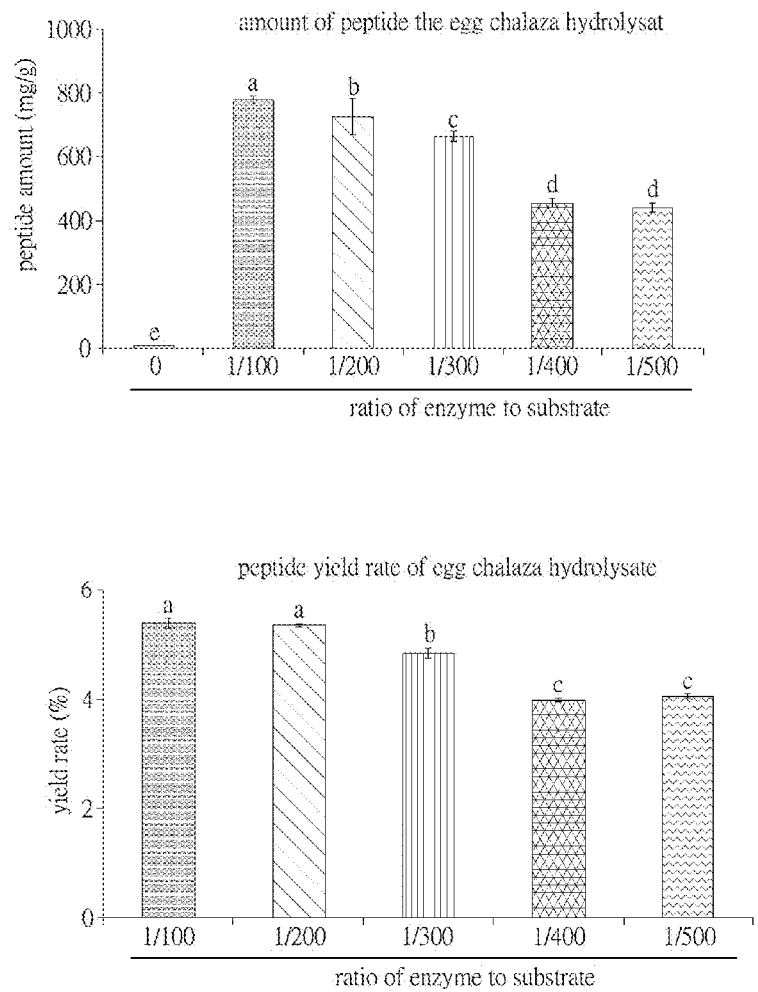
FIG. 4 shows bar charts of a peptide amount and a yield rate of an egg chalaza hydrolysate according to the present invention.

Refer to FIG. 4, the amount of peptide in the unhydrolyzed egg chalazae contained is 6.42 mg/g. After hydrolysis by PA, the amount of peptide contained in the PA hydrolysate is significantly increased. The PA hydrolysate group with the highest ratio of enzyme to substrate (1:100) has the highest amount of peptide-778.65 mg/g. Then the amount of peptide the PA hydrolysate contained is reduced along with the decreasing enzyme to substrate ratio. After 0.5 hour hydrolysis, the peptide yield rate of the egg chalaza hydrolysate with higher to lower different enzyme to substrate ratio is 5.37%, 5.35%, 4.83%, 3.99%, and 4.04% in turn. The yield rate is calculated by the following equation:

Yield rate (%)=(weight of egg chalaza hydrolysate (g)/weight of egg chalaza (g))×100%

According to results of the experiment two and the experiment three, the egg chalaza hydrolysate with higher amount of peptide and better antioxidant activity is prepared by protease A with the ratio of enzyme to substrate 1:100 and 0.5 hour hydrolysis.

EXPERIMENT FOUR

Component Analysis of Egg Chalaza Hydrolysate 4.1 Sodium Dodecyl Sulfate Polyacrylamide Gel Electrophoresis (SDS-PAGE) Analysis SDS-PAGE is used to evaluate degree of protein hydrolysis and distribution of protein segments. A test sample and a molecular-weight size marker are injected into sample wells of the gel ready for SDS-PAGE and electrophoresis is performed. Then the gel is placed into a staining solution containing 0.25% Coomassie brilliant blue and a destaining solution (10% acetic acid and 50% methanol) in turn. At last take a picture of the gel.

Figure 5:
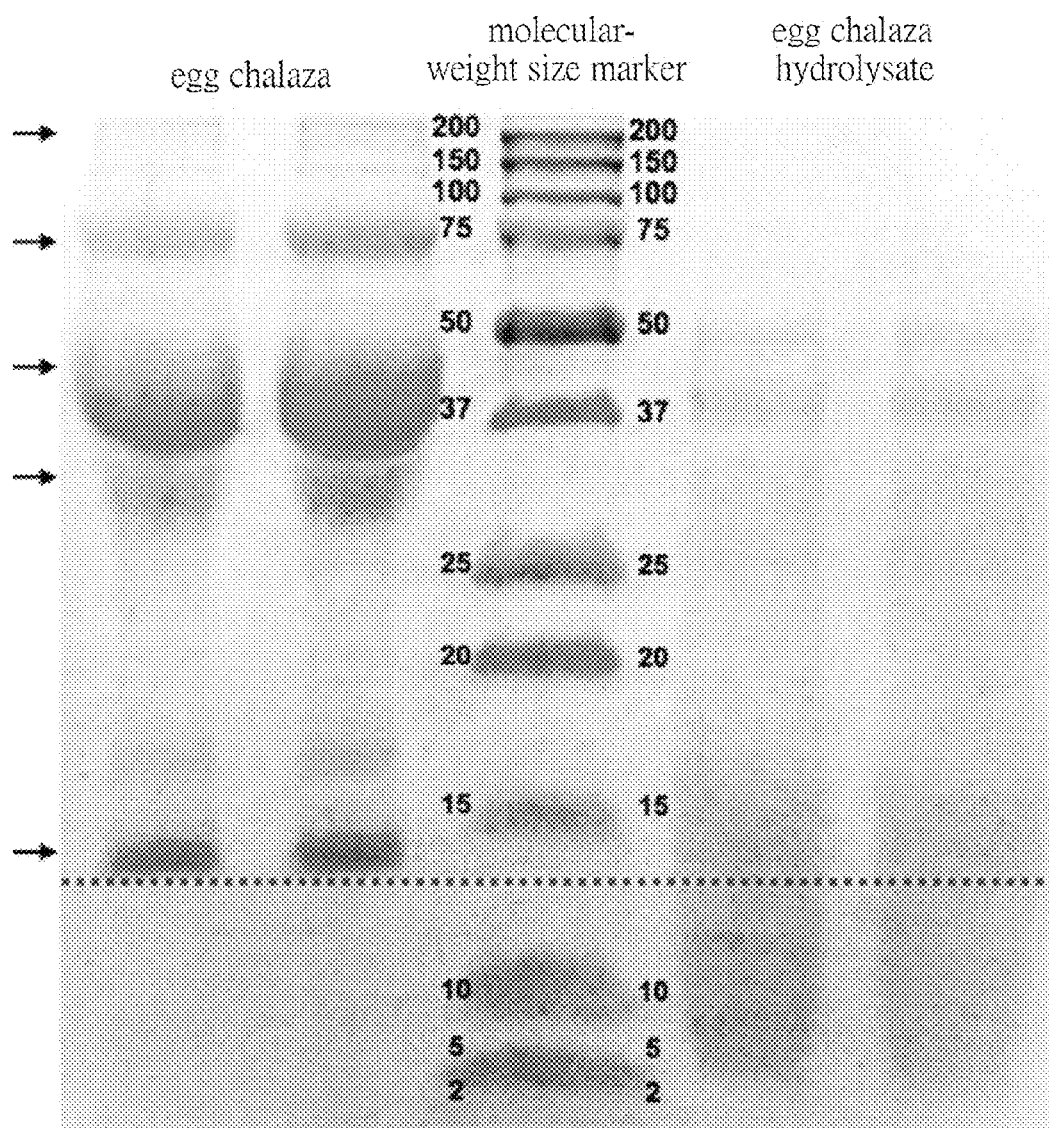
FIG. 5 shows unhydrolyzed egg chalaza and an egg chalaza hydrolysate analyzed by SDS-PAGE according to the present invention.

As shown in FIG. 5, several kinds of large protein segments in the unhydrolyzed egg chalaza are detected, as the arrows indicate. After hydrolysis with protease A, nearly all protein segments whose molecular weight are larger than 50 kDa disappeared and smaller protein segments (<14 kDa) are detected. The result shows that large protein segments are hydrolyzed and decomposed once the egg chalaza being hydrolyzed by protease A.

4.2 Analysis on Content of Free Amino Acids and Short Chain Peptides Contained in Egg Chalaza Hydrolysate The analysis is entrusted to Food Industrial Research and Development Institute (HsinChu Taiwan). Methods for amino acid analysis is involve in the use of trichloroacetic acid (TCA) as an extraction solvent (Konosu et al., 1974) for getting the test samples. 5 g of test sample is mix with 20 mL 7% TCA solution and reacts for 2 minutes. Then the test sample-TCA solution is centrifuged at 4000 g, 4° C. for 20 minutes. The supernatant if the test sample-TCA solution is filtered through filter paper and the volume if the filtrate is adjusted to 100 mL with 7% TCA to get a TCA mixed solution. 40 mL of TCA mixed solution is mixed with the same volume of alcohol, and a Remove a water layer is removed after vacuum concentration. At last, the total volume is brought to 25 mL with distilled deionized water (ddH$_2$O), and get a TCA soluble extract. 1 mL TCA soluble extract is diluted with 0.02 N HCl and filtered with a 0.2 μm film, and the amino acid content of the TCA soluble extract is analyzed with an amino acid analyzer (Hitachi L8800 amino acid analyzer, Hitachi High-Technologies Co., Tokyo, Japan).

Table 2 shows the analysis results on content of free amino acids and short chain peptides of unhydrolyzed egg chalaza and PA hydrolysate are revealed. The results show that the free amino acid is increased from 39.14 mg/100 g in the unhydrolyzed egg chalaza to 10,827.77 mg/100 g in the PA hydrolysate. The PA hydrolysate is composed of leucine, arginine, phenylalanine, valine, and lysine that are 15.47 wt %, 10.89 wt %, 9.74 wt %, 9.64 wt % and 9.09 wt % of the total free amino acids respectively. Moreover, the amount of anserine and carnosine is also changed from not detected before hydrolysis to 48.06 mg/100 g and 106.84 mg/100 g after hydrolysis. Thus the analysis results confirm that the content of free amino acids and short chain peptides in hydrolysates are significantly increased by optimum conditions used in the present invention.

TABLE 2

| Free amino acids | egg chalaza (mg/100 g dry powder) | PA hydrolysate (mg/100 g dry powder) |
|---|---|---|
| L-Leucine | 3.01 | 1675.41 |
| L-Arginine | — | 1179.76 |
| L-Phenylalanine | 6.96 | 1054.68 |
| L-Valine | 4.73 | 1044.22 |
| L-Lysine | — | 984.47 |
| L-Isoleucine | 0.72 | 737.49 |
| L-Methionine | 0.58 | 532.24 |
| L-Threonine | — | 423.57 |
| Tryptophan | — | 267.21 |
| L-Histidine | — | 350.01 |
| Total essential amino acids | 16 | 8249.06 |
| Asparagine | — | 473.56 |
| L-Tyrosine | 0.36 | 456.55 |
| L-Serine | 0.77 | 452.43 |
| o-Phosphoserine | 3.33 | 231.69 |
| L-Glutamic acid | 0.52 | 179.67 |
| L-Aspartic acid | 0.70 | 118.24 |
| Glycine | 3.21 | 141.41 |
| L(−)-Proline | — | 76.73 |
| L-2-aminoadpic acid | — | 75.40 |
| DL-3-Aminoisobutyric acid | — | 72.70 |
| γ-Aminobutyric acid | — | 66.07 |
| L-Ornithine | 12.51 | 61.41 |
| β-Alanine | — | 42.53 |
| L-Cystathionine | 0.23 | 37.25 |
| Sarcosine | — | 32.44 |
| DL-plus allo-σ-Hydroxylysine | 1.51 | 20.17 |
| Ethanol amine | — | 5.05 |
| Total non-essential amino acids | 23.14 | 2578.71 |
| L-Carnosine | — | 48.06 |
| L-Anserine | — | 106.84 |

EXPERIMENT FIVE

Application of the Egg Chalaza Hydrolysate to Reduction of Alcohol-Induced Liver Injury 5.1 Laboratory Animal Eighteen 8-week male C57BL/6 mice from Laboratory animal center of National Taiwan University College of Medicine are placed in an animal room at 22±2° C., and 60-80% relative humidity with a 12-hour light/12-hour dark cycle. The 18 mice are divided into three groups randomly.
(1) Control group (CON): free access to normal liquid diet and daily tube-feeding with 0.1 mL normal saline solution
(2) Alcohol group (ALC): free access to Lieber-DeCarli liquid diet containing ethanol and daily tube-feeding with 0.1 mL normal saline solution
(3) The egg chalaza hydrolysate group (ALC+PA hydrolysate): free access to Lieber-DeCarli liquid diet containing ethanol and daily tube-feeding with 0.1 mL egg chalaza hydrolysate (100 mg PA hydrolysate/kg body weight)

TABLE 3 composition of normal liquid diet and Lieber-DeCarli liquid diet containing ethanol

| Composition | normal liquid diet (g/L) | Lieber-DeCarli liquid diet containing ethanol (g/L) |
|---|---|---|
| Casein | 41.40 | 41.40 |
| L-Cystine | 0.50 | 0.50 |
| DL-Methionine | 0.30 | 0.30 |
| corn oil | 8.50 | 8.50 |
| olive oil | 28.40 | 28.40 |
| safflower oil | 2.70 | 2.70 |
| Maltodextrin | 115.20 | 25.60 |

TABLE 3-continued composition of normal liquid diet and Lieber-DeCarli liquid diet containing ethanol

| Composition | normal liquid diet (g/L) | Lieber-DeCarli liquid diet containing ethanol (g/L) |
|---|---|---|
| Cellulose | 10.00 | 10.00 |
| salt mixture | 8.75 | 8.75 |
| Vitamin mixture | 2.50 | 2.50 |
| Choline | 0.53 | 0.53 |
| Xantan Gum | 3.00 | 3.00 |
| Formulation | 221.78 g above mixture dissolved in 1 L | 132.18 g above mixture added with 67.3 mL 95% ethanol and brought the total volume to 1 L with water |
| Calorie | 1.0 Kcal/mL (35% from lipid, 47% from carbohydrate and 18% from protein) | 1.0 Kcal/mL (35% fat-derived, 11% carbohydrate-derived, 18% protein-derived, and 36% derived from ethanol) |

After one-week adaptation period in the animal room, the mice are tested for 8 weeks. All mice are sacrificed at the $9^{th}$ week and their blood samples, liver samples and stool samples are collected respectively for further analyses. The stool of the mice is collected one week before being killed and is dried in the oven for storage. The diet is removed the night before the end of the experiment, and the mice were fasted for 8 hours. The blood was collected by capillary tubes and was placed on ice for an hour, then centrifuged at 2500 g and 4° C. for 10 minutes, and the step was repeated to get mice serum. After being sacrificed, the weight of the mice heart, liver, kidney and abdominal fat were recorded. All the samples collected including serum, stool and organs were stored in a −80° C. freezer for the further analyses.

The design structure of this research is a Completely Randomized Design. The data is analyzed by one way analysis of variance (ANOVA) by SAS9.2 software. Once there is significant differences among groups ($p<0.05$), use LSD (least significant difference) for comparing treatment group means. Results are shown in mean±standard deviation (mean±SD). In the analysis charts, the two groups without significant difference are classified into the same group and labeled/marked with the same small letter. If some groups are labeled with ab means there is no significant difference between these groups and the group a or group b. Thus they are classified into both the group a and the group b.

5.2 Evaluation of Physical Indices of Mice
(1) Physiological Indices

After sacrifice, body weight, organ weight, and intraabdominal fat pad weight of the mice are measured, and the weight of organs or tissues are presented as relative weight to the body weight. The relative weight is calculated by dividing the weight of organ/tissue by the body weight (relative weight/100 g-body weight). The results are shown in Table 4. At the first week of the experiment, when mice are just being separated, there is no significant difference in body weight among the groups ($p>0.05$, data not shown). After 8 weeks, the average body weight of the ALC group is 23.86 g. Compared with the CON group, the average body weight of the ALC group is increased. Compared with the ALC group, the final body weight of the ALC+PA hydrolysate group is decreased significantly ($p<0.05$), with the average body weight of 19.73 g. There is no significant difference ($p>0.05$) in the body weight between the ALC+PA hydrolysate group and the CON group. As to the analysis of the relative size of organs, there is no significant difference ($p>0.05$) in the relative weight of kidney and heart among the three groups. But the relative weight of liver and the relative weight of intra-abdominal fat pad in the ALC group are obviously higher than those of the CON group ($p<0.05$). Compared with the CON group, the relative weight of liver of the ALC+PA hydrolysate group is reduced and the relative weight of the intra-abdominal fat pad of the ALC+PA hydrolysate group is obviously decreased ($p<0.05$).

TABLE 4

|  | CON (control group) | ALC (alcohol group) | ALC + PA (Egg chalaza hydrolysate group) |
|---|---|---|---|
| body weight | 21.84 ± 0.33ab | 23.86 ± 1.24a | 19.73 ± 2.78b |
| relative weight (g/100 g-body weight) | | | |
| Heart | 0.51 ± 0.02a | 0.48 ± 0.03a | 0.50 ± 0.05a |
| Liver | 4.06 ± 0.32b | 4.87 ± 0.28a | 4.32 ± 0.72ab |
| Kidney | 1.27 ± 0.11a | 1.24 ± 0.15a | 1.27 ± 0.18a |
| intra-abdominal fat pad | 1.19 ± 0.23b | 2.99 ± 0.33a | 0.93 ± 1.03b |

(2) Liver Injury and Blood Lipid

Asparate aminotransferase (AST), alanine aminotransferase (ALT), alkaline phosphatase (ALP) are rich in the liver, and will be released in to the blood once liver cells are injured. Thus serum AST, ALT and ALP levels are used as indicators to access the hepatic injury. Besides lipid disorder, chronic alcohol consumption also causes dyslipidemia. Thus changes in serum lipid level are also monitored for analysis of the effect of PA hydrolysate on blood biochemical indices of mice with chronic alcohol exposure. Serum triglyceride (TG) and total cholesterol (TC) of the mice are detected by an automated dry chemistry analyzer (Spotchem™ II, Arkray Inc., Kyoto, Japan) with test papers.

Refer to Table 5, AST, ALT and ALKP of the ALC group are all significantly higher than those of the CON group ($p<0.05$). After supplement of PA hydrolysate (ALC+PA hydrolysate group), these content of serum AST, ALT and ALKP is reduced compare with the ALC group, and has no difference with the CON group ($p>0.05$). The measurements of the liver enzymes infer that chronic alcohol consumption for 8 weeks do causes mice liver injury while the supplement of PA hydrolysate could reduce, even alleviate liver injury caused by chronic alcohol consumption. Moreover, the TG and TC levels of the ALC group are obviously higher than those of the CON group ($p<0.05$). The supplement of PA hydrolysate in the ALC+PA hydrolysate group can reduce the content of serum TG and TC effectively ($p<0.05$) compare with the ALC group, and the content of serum TG and TC hase no different with the CON group ($p>0.05$).

TABLE 5

|  | CON group | ALC group | ALC + PA group |
|---|---|---|---|
| AST (unit/L) | 123.5 ± 11.32b | 185.13 ± 36.51a | 120.00 ± 40.10b |
| ALT (unit/L) | 23.00 ± 2.23b | 86.00 ± 2.45a | 25.20 ± 3.27b |
| ALKP (unit/L) | 72.60 ± 8.88b | 89.80 ± 21.92a | 64.00 ± 28.14b |
| TG (mg/dL) | 92.80 ± 3.11b | 105.00 ± 9.54a | 92.00 ± 2.83b |
| TC (mg/dL) | 83.60 ± 0.55b | 117.80 ± 16.41a | 81.08 ± 17.61b |

(3) Histopathological Observations of Mice Liver

Figure 6:
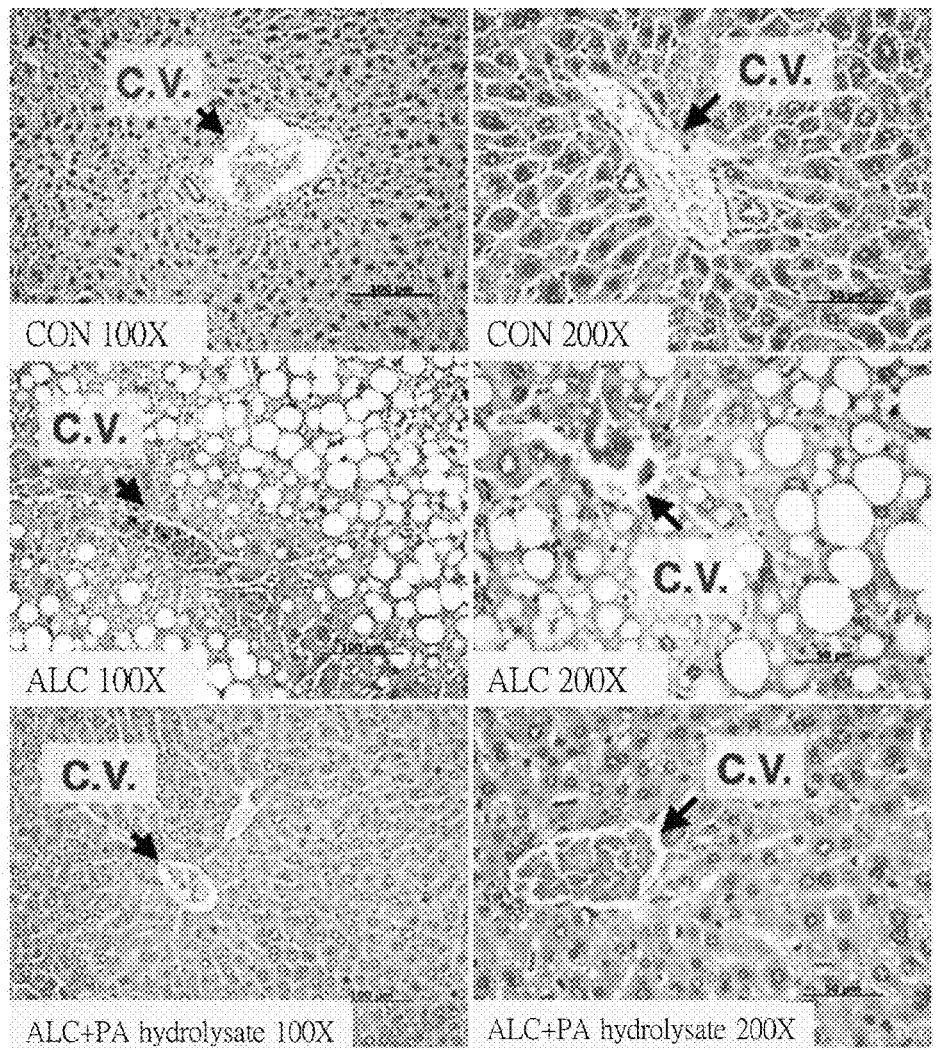
FIG. 6 shows mouse liver biopsies with hematoxylin-eosin stain (H&E stain) according to the present invention.

Chronic alcohol consumption leads to macrovesicular fatty liver and the morphology changes can be observed by hematoxylin-eosin stain (H&E stain). Refer to FIG. 6, there are a lot of large lipid droplets around the central vein (C.V.) in mice liver biopsy of the ALC group. This is typical characteristic of the macrovesicular fatty liver. As to the mice fed with PA hydrolysate, the liver morphology of the liver biopsy shows no significant different with that of the CON group. Thus the PA hydrolysate do reduces hepatic lipid accumulation caused by chronic alcohol intake.

(4) Lipid Level in Mouse Livers and Feces

Figure 7:
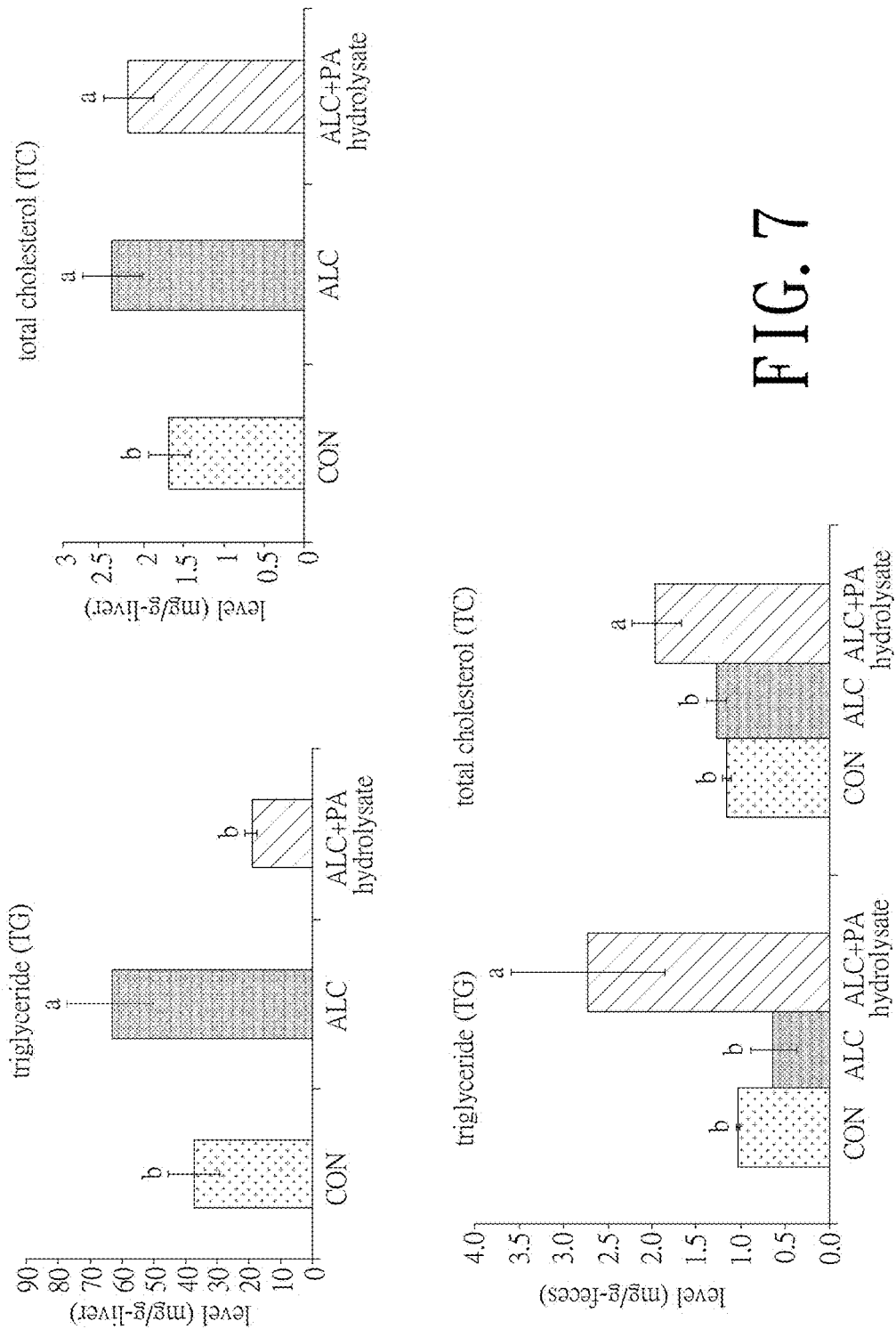
FIG. 7 shows triglyceride and total cholesterol levels in mouse liver and stool respectively according to the present invention.

In order to learn more about hepatic lipid accumulation, the mice were sacrificed and the lipids of livers were extraction and the contents of TG and TC were analysis. Refer to FIG. 7, the TG and TC levels in the liver of the ALC group are significantly higher than those of the CON group ($p<0.05$). After being given with the PA hydrolysate, the TG level in the liver of the ALC+PA hydrolysate group is decreased significantly compared with the CON group ($p<0.05$). The reduced TG level has no significant difference with the CON group ($p>0.05$). Moreover, the TC level in the liver of the ALC+PA hydrolysate group is also reduced compared with the CON group. As to the lipid level in feces, the TG and TC levels in the feces of the ALC+PA hydrolysate group are significantly higher than those of the CON group and the ALC group ($p<0.05$). This implies that the PA hydrolysate can reduce lipid absorption or accelerate excretion of lipid.

(5) Expression of of Lipid Homeostasis-Related Genes in Mice

Figure 8:
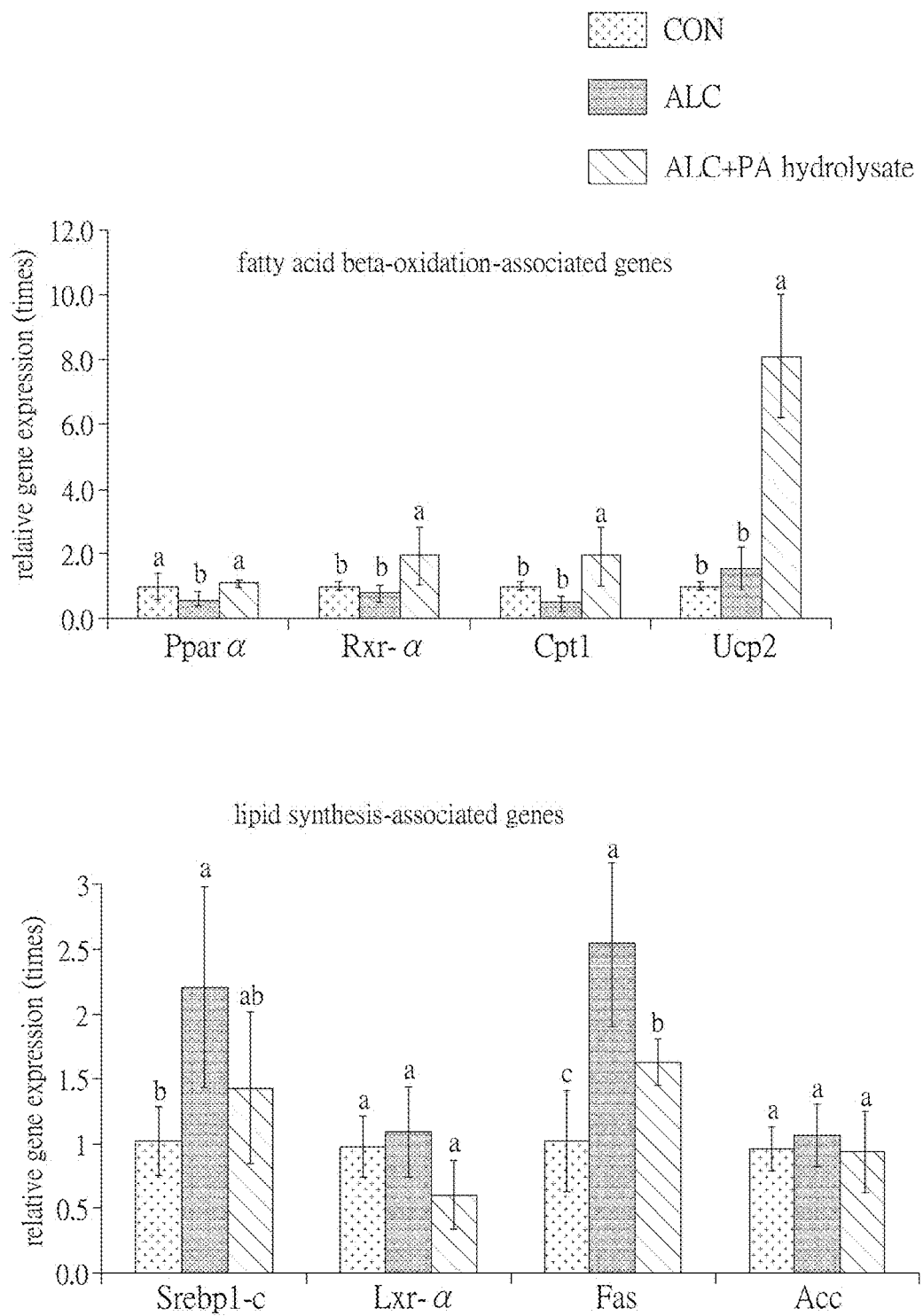
FIG. 8 shows expression of lipid homeostasis-associated genes in mice according to the present invention.

In order to evaluate the effect of PA hydrolysate on expression of lipid homeostasis-related genes in mice, the extract mRNA of mice liver tissue is extracted and analyzed. The expressions of genes associated with fatty acid beta-oxidation and lipid synthesis are analysed by real time quantitative polymerase chain reaction (qRT-PCR). The genes associated with fatty acid beta-oxidation include Peroxisome proliferator-activated receptor α (Pparα) gene, Retinoid X receptor α (Rxr-α) gene, Carnitine palmitoyltransferase I (Cpt1) gene, and Uncoupling protein 2 (Ucp2) gene. The genes associated with lipid synthesis include Sterol regulatory element-binding protein (Srbp1-c) gene, Liver X receptor alpha (Lxr-α) gene, Fatty acid synthase (Fas) gene and Acetyl-CoA carboxylase (Acc) gene. Refer to FIG. 8, expression of Pparα in the ALC group is significantly lower than that in the CON group ($p<0.05$). Both Rxr-α and Cpt1 expressions are also decreased. After being given with PA hydrolysate, expressions of genes associated with beta-oxidation, Pparα, Rxr-α, Cpt1, and Ucp2 in mice liver are all increased significantly ($p<0.05$). Compare with the CON group, expressions of Srebp-1c and Fas in the ALC group are significantly increased ($p<0.05$), and expressions of Lxr-α and ACC dose not significantly increase ($p>0.05$). After supplement of PA hydrolysate, expressions of Srebp-1c, Lxr-α and Acc in mice liver are declined compared with the ALC group while expression of Fas is dramatically decreased ($p<0.05$).

(6) Evaluation of Antioxidant Activity of Mice Serum and Liver

ABTS$^+$ radical scavenging activity is measured for an evaluation of antioxidant activity of mouse serum and liver and trolox equivalent antioxidant capacity (TEAC) of mouse serum or liver is calculated. The unit is Trolox Equivalents (TE), e.g. mol TE per each unit of weight of sample. Thiobarbituric acid reactive substances (TBARS) assay is used to detect lipid peroxidation in the mice. At last, the concentration of enzymes of the antioxidant defense system in mouse liver such as superoxide dismutase (SOD), catalase (CAT), glutathione peroxidase (GPx), and glutathione (GSH) are also detected.

Figure 9:
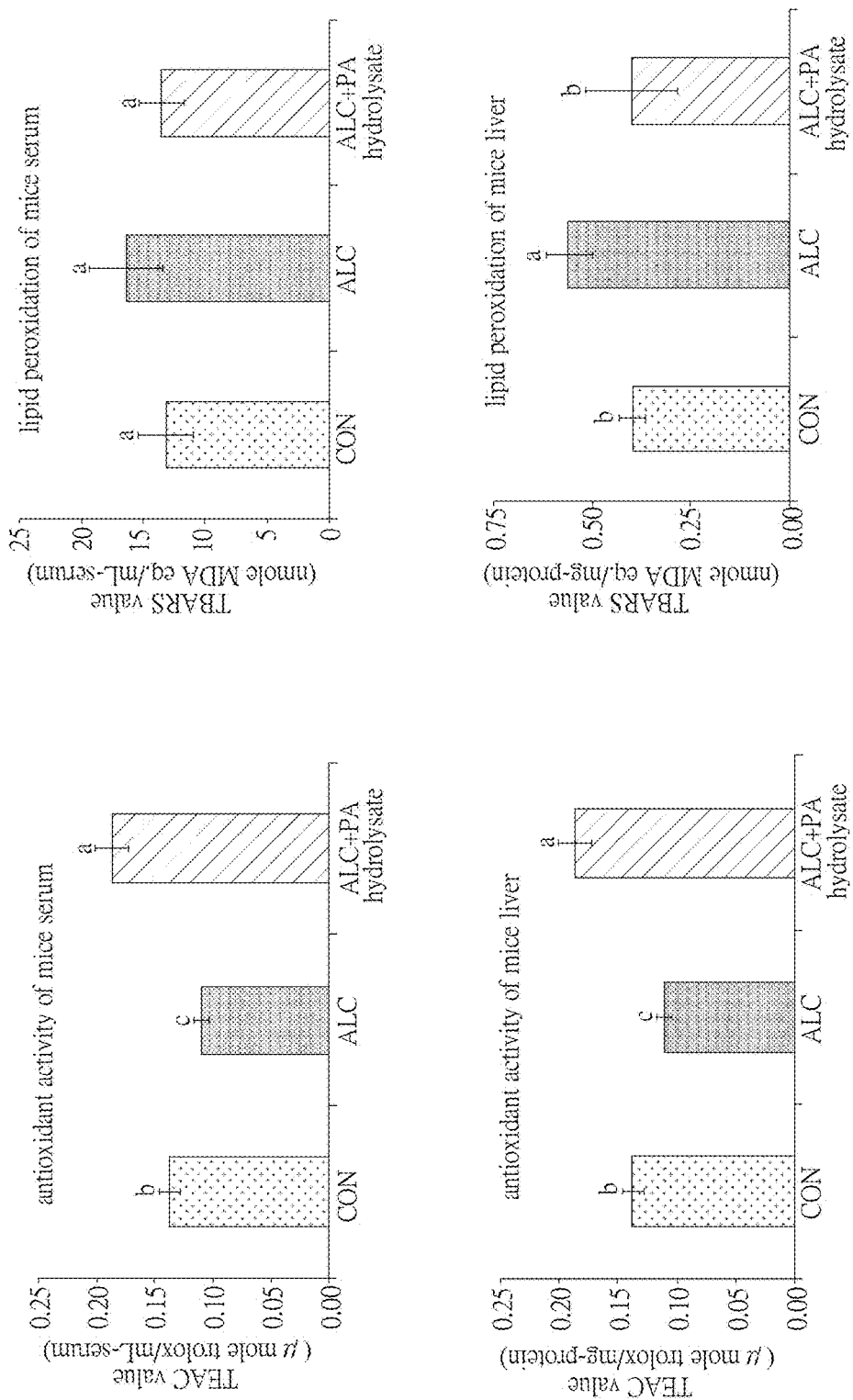
FIG. 9 shows analysis results of total antioxidant ability and lipid peroxidation in mice serum and liver according to the present invention.

Refer to FIG. 9, after 8-week chronic alcohol consumption (the ALC group), serum TEAC in mice is obviously lower than that of the CON group ($p<0.05$) while serum TBARS shows an upward tendency. After supplement of the PA hydrolysate, serum TEAC in mice is significantly increased ($p<0.05$) compare with the ALC group, and is even higher than the CON group. Serum TBARS seems to return to the original level in the ALC+PA hydrolysate group. Moreover, liver TEAC of the ALC group with chronic alcohol consumption is 0.11 μmole TE/mg-protein, obviously lower than 0.14 μmole TE/mg-protein of the CON group ($p<0.05$). Liver TBARS of the ALC group is 0.55 nmole MDA eq./mg-protein, significantly higher than 0.40 nmole MDA eq./mg-protein of the CON group. The above results show that alcohol consumption reduces antioxidant activity and increases lipid peroxidation of liver tissues. By supplement of PA hydrolysate, liver TEAC is up to 0.18 μmole TE/mg-protein, significantly higher than the rest two groups ($p<0.05$) while liver TBARS is obviously lower than the ALC group ($p<0.05$) and turns back to the same level as the CON group when supplement of PA hydrolysate. Thus the serum or liver antioxidant activity is increased while lipid peroxidation in serum or liver is inhibited once the mice treated with alcohol being given with PA hydrolysate.

Figure 10:
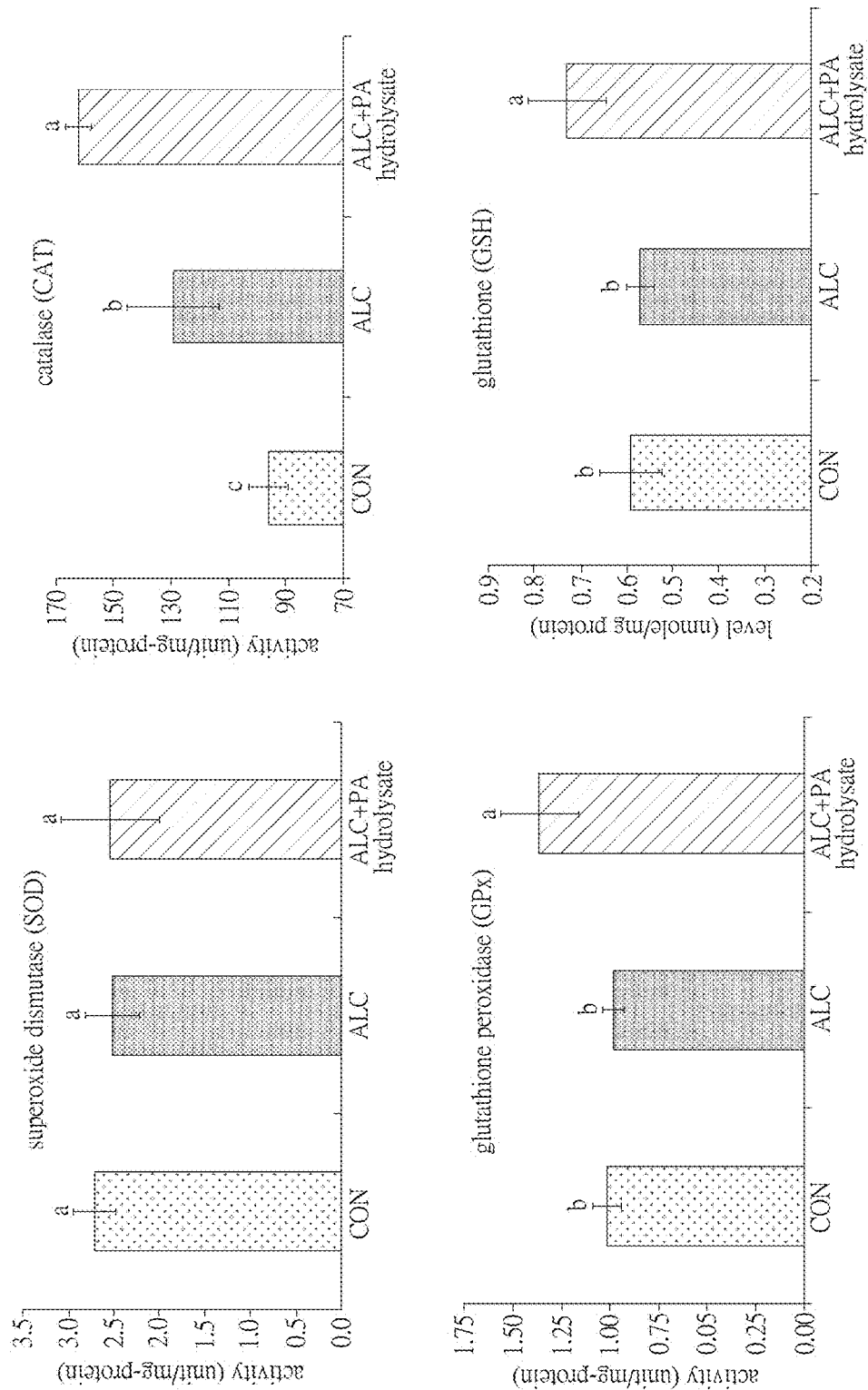
FIG. 10 are bar charts showing the activities of antioxidant enzymes including superoxide dismutase (SOD), catalase (CAT), and glutathione peroxidase (GPx), and glutathione (GSH) in mice livers according to the present invention.

Refer to FIG. 10, the SOD activity in mouse liver is measured and no significant difference is observed among the three groups ($p>0.05$). The CAT activity of the CON group is 96.17 unit/mg-protein while the CAT activity of the ALC group is rising to 129.16 unit/mg-protein significantly ($p<0.05$). The CAT activity of the ALC+PA hydrolysate group is increased up to 162.20 unit/mg-protein, obviously higher than the rest two groups ($p<0.05$). The GPx activity in the CON group is 1.01 unit/mg-protein and has no significant difference with the GPx activity in the ALC group (0.98 unit/mg-protein) ($p>0.05$). After supplement of PA hydrolysate, the GPx activity in the liver is significantly improved, up to 1.36 unit/mg-protein ($p<0.05$). The reduced GSH level of the ALC group is reduced compared with the CON group. As to the ALC+PA hydrolysate group having supplement of PA hydrolysate, the reduced GSH level in liver is significantly improved and higher than the rest two groups ($p<0.05$).

(7) Analysis of Severity of Liver Inflammation in Mice

Figure 11:
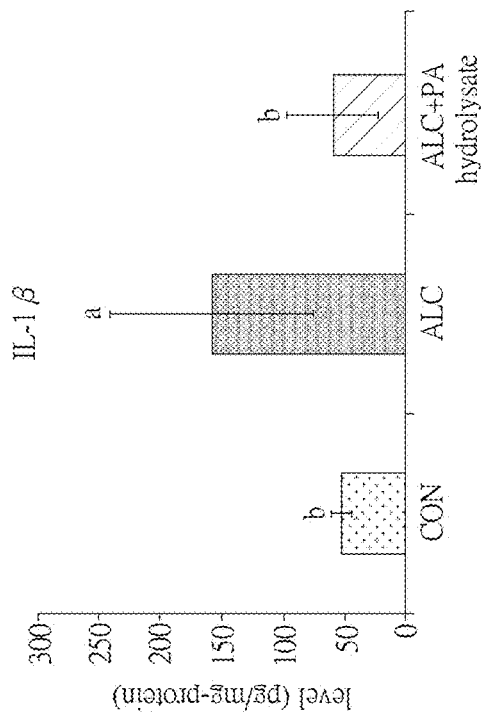
FIG. 11 are bar charts showing inflammatory cytokines levels in the mouse liver according to the present invention.
Figure 11:
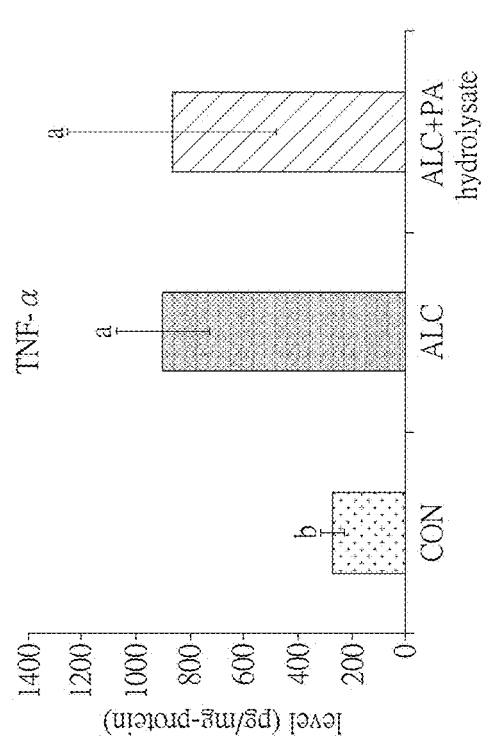
Figure 11:
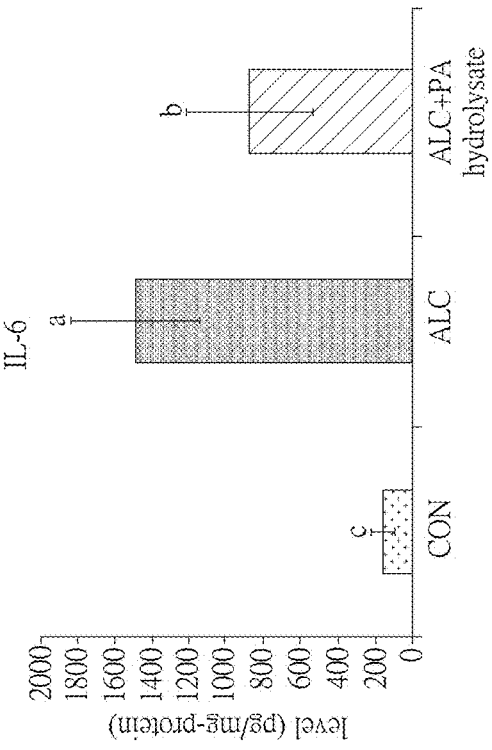

Long-term alcohol consumption leads to chronic liver inflammation. The effect of PA hydrolysate on the severity of liver inflammation can be evaluated by analysis of concentration changes in common inflammatory factors including tumor necrosis factor-α (TNF-α), interleukin-1β (IL-1β) and interleukin-6 (IL-6). Refer to FIG. 11, the TNF-α, IL-1β, and IL-6 levels in the mice liver of the ALC group are all significantly higher than those of the CON group ($p<0.05$). After being given with PA hydrolysate, the TNF-α level is not reduced ($p>0.05$) but the IL-1β and IL-6 levels are dramatically decreased compared with the ALC group ($p<0.05$). This means the PA hydrolysate can reduce inflammation caused by chronic alcohol consumption.

Compared with the techniques available now, the present invention has the following advantages:

1. The egg chalaza hydrolysate of the present invention includes a lot of free amino acids, carnosine and anserine compared with unhydrolyzed egg chalaza 2. The egg chalaza hydrolysate of the present invention has good in vitro antioxidant activity, including good free radical scavenging activity and ferrous ion chelating ability.

3. The egg chalaza hydrolysate of the present invention can reduce serum lipid level. Both serum triglyceride (TG) and total cholesterol (TC) are decreased effectively.

4. The egg chalaza hydrolysate of the present invention helps reduce fat accumulation in livers and hepatic oxidative stress in livers.

5. The egg chalaza hydrolysate of the present invention has anti-inflammatory effect on the liver, able to reduce secretion of inflammatory factors related to livers such as IL-1β, IL-6, etc.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A method for preparing an egg chalaza hydrolysate comprising the steps of:

step 1: defrosting an egg chalaza and washing with distilled deionized water for removal of impurities; taking a first product at a lower layer after centrifugation;

step 2: heating the first product at 95° C. for 10-30 minutes and cooling down; then adding distilled deionized water to get a homogeneous solution of the egg chalaza;

step 3: mixing 100-200 g homogeneous solution of the egg chalaza with a hydrolase at a ratio of 100:1-500:1 (w/w) and getting a first hydrolysate solution after reacting a period of time;

step 4: heating the first hydrolysate solution at 95° C. for 10-30 minutes and cooling down; then taking a second hydrolysate solution at an upper layer after centrifugation; and step 5: filtering and lyophilizing the second hydrolysate solution to get the egg chalaza hydrolysate.

2. The method as claimed in claim 1, wherein the hydrolase is selected from the group consisting of pepsin, protease A, and prozyme 6; an enzyme-to-substrate ratio is 1:200 (w/w) and the period of time is 30 minutes.

3. The method as claimed in claim 2, wherein the hydrolase is protease A.

* * * * *